(12) United States Patent
Elkins et al.

(10) Patent No.: US 7,048,939 B2
(45) Date of Patent: *May 23, 2006

(54) METHODS FOR THE INHIBITION OF NEOINTIMA FORMATION

(75) Inventors: Christopher J. Elkins, Redwood City, CA (US); Michael D. Dake, Stanford, CA (US); Jacob M. Waugh, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 228 days.

This patent is subject to a terminal disclaimer.

(21) Appl. No.: 10/101,453

(22) Filed: Mar. 11, 2002

(65) Prior Publication Data

US 2002/0193336 A1    Dec. 19, 2002

Related U.S. Application Data

(60) Provisional application No. 60/285,383, filed on Apr. 20, 2001.

(51) Int. Cl.
*A61F 2/00* (2006.01)
*A61F 2/06* (2006.01)
*A61K 31/44* (2006.01)

(52) U.S. Cl. ............... 424/423; 623/1.42; 514/291

(58) Field of Classification Search ............ 623/1.42, 623/1.39; 424/422–426; 514/291
See application file for complete search history.

(56) References Cited

U.S. PATENT DOCUMENTS

| 5,782,908 A | * | 7/1998 | Cahalan et al. ............. 623/1.13 |
| 5,916,597 A | * | 6/1999 | Lee et al. ................... 424/501 |
| 6,096,070 A |   | 8/2000 | Ragheb et al. |

FOREIGN PATENT DOCUMENTS

| EP | 0747069 A2 | 12/1996 |
| EP | 0747069 A3 | 12/1996 |
| EP | 0 950 386 A2 * | 10/1999 |

OTHER PUBLICATIONS

Ettenson, D. et al., Local Drug Delivery: An Emerging Approach in the Treatment of Restenosis, Vascular Medicine, (2000), vol. 5: 97-102.
Gunn, J. et al., Stent Coatings and Local Drug Delivery State of the Art, European Heart Journal, (1999), vol. 20: 1693-1700.
Raman, K. et al., Coated Stents: Local Pharmacology, Semin Intervent Cardiol, (1998), vol. 3: 133-137.

* cited by examiner

*Primary Examiner*—Celian Qian
*Assistant Examiner*—Quang Nquyen
(74) *Attorney, Agent, or Firm*—Pamela J. Sherwood; Bozicevic, Field, & Francis LLP (57) ABSTRACT

Restenosis is inhibited through local delivery of anti-restenotic agents including angiotensin converting enzyme inhibitors; nicotine receptor agonists, agents that increase concentrations of nitric oxide, anti-angiogenic agents, agonists of the TGF-beta receptor; death domain receptor ligands; and thrombin inhibitors. In one embodiment of the invention, the localized delivery is effected through the use of a stent modified for delivery of the agent at the site of injury from balloon angioplasty.

30 Claims, 3 Drawing Sheets

METHODS FOR THE INHIBITION OF NEOINTIMA FORMATION

CROSS-REFERENCE TO RELATED APPLICATIONS

This application claims the benefit of priority from U.S. Provisional application 60/285,383, filed Apr. 20, 2001, herein incorporated by reference.

BACKGROUND OF THE INVENTION

Cardiovascular disease remains by far the leading cause of death in Western nations and carries an unparalleled health and economic burden. Treatment by balloon angioplasty (percutaneous transluminal angioplasty, or PTA) has been shown to improve life expectancy, but although an alternative to bypass surgery for relieving stenosis of obstructive atherosclerotic blood vessels, the long-term success of the angioplasty is often compromised by the onset of restenosis, thereby requiring reintervention.

In the PTA procedure, an inflatable balloon disposed at the distal end of a catheter is positioned in the region of a stenosis. The balloon is inflated under fluid pressure to reconfigure the narrowed lumen and thereafter permit increased blood flow through the affected artery. It is not unusual that inflation-deflation cycles will be repeated, several times where the narrowing is severe. This mechanical violence to the arterial wall may produce the desired opening of the artery, but in delayed consequence the procedure is followed by an estimated 25%–50% incidence of restenosis, typically within 6 months to 2 years of the procedure (depending on the location), at or near the injured site.

Serial intravascular ultrasound studies have shown that restenosis after stent deployment is due almost entirely to smooth muscle hyperplasia and matrix proliferation. In-stent neointima formation thus remains a major procedural limitation for stent use, limiting both utilization and long-term clinical benefits.

Vessel injury, such as endothelial denudation, injury to the vascular wall, and rupture of the vase vasorum, can result as an unwanted consequence to an angioplasty thereby making the treated site susceptible to restenosis. Upon injury, the ensuing deposition of platelets, in connection with the vessel's healing mechanism, signals smooth muscle cell proliferation within the arterial wall. The deposition of platelets may lead to acute thrombosis in some circumstances. More significantly, the proliferation of smooth muscle cells is a process which frequently continues unabated and has therefore been widely implicated as a prominent factor in the resulting restenosis. No pharmacologic or mechanical intervention has heretofore proven sufficiently effective in preventing restenosis following angioplasties.

Relevant Art. Recent advancements have demonstrated that controlled release platforms can be employed to predictably deliver drugs locally in vivo without additional damage from the materials themselves. These strategies offer the potential to create defined release curves for multiple drugs by combining different materials. Localized drug administration is particularly advantageous where drug retention in the treated locus is required for an effective period of time without appreciably affecting other body tissues.

Reviews of the field of local drug delivery, and the treatment of restenosis may be found in Ettenson and Edelman (200) *Vasc Med* 5(2):97–102; Gunn and Cumberland (1999) *Eur Heart J* 20(23):1693–700; and Raman and Edelman (1998) *Semin Interv Cardiol* 3(3–4):133–7; among others.

SUMMARY OF THE INVENTION

Compositions and methods are provided for preventing restenosis through local delivery of anti-restenotic agents. In one embodiment of the invention, the localized delivery is effected through the use of a drug delivery stent. One stent of interest is a; channeled stent comprising a matrix, where the matrix has entrapped the anti-restenotic agent. The matrix resides within the channels, and stent and matrix are encased with a gel covalently bound to the stent surface, which prevents loss of the matrix during transport and implantation of the stent.

BRIEF DESCRIPTION OF THE DRAWINGS

FIGS. 2A, 2B and 2C are photographs depicting early in-stent plaque formation. Representative photos were taken at midpoint between stent struts for rabbit aortas 7 days after deployment of (5A) Palmaz-Schatz stent (P-S), (5B) stent containing microspheres and anchored PEG-methacrylate gel (MS-gel), or (5C) MS-gel platform containing a nitric oxide donor as a therapeutic anti-restenotic agent (MS-gel-tx).

DETAILED DESCRIPTION OF THE EMBODIMENTS

Compositions and methods are provided for preventing restenosis through local delivery of anti-restenotic agents. Specific agents useful as anti-restenotic agents include angiotensin converting enzyme inhibitors; nicotine receptor agonists, agents that increase concentrations of nitric oxide, anti-angiogenic agents, agonists of the TGF-beta receptor; death domain receptor ligands; rapamycin; antiplatelet agents; GPIIb/IIIa inhibitors; DNA; ribozymes; RNA; and thrombin inhibitors. In one embodiment of the invention, the localized delivery is effected through the use of a stent modified for delivery of the agent at the site of injury from balloon angioplasty.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a microsphere" includes a plurality of such microspheres and reference to "the stent" includes reference to one or more stents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Restenosis: Several clinical definitions of restenosis are available. The condition may be defined as a reduction of minimal luminal diameter in a vessel to less than 50% of the normal lumen diameter, or loss of at least 50% of the initial gain achieved in angioplasty. Another useful measure of restenosis is the ratio of intimal area to medial area of a vessel after a suitable period of time, usually at least about 2 weeks after initiation of treatment, more usually at least about 4 weeks after initiation of treatment. The anti-restenotic agents used in the methods of the invention provide for a statistically significant reduction on the intimal/medial ratio as compared to a control treatment in which the anti-restenotic agents agent is not present. Usually the decrease in intimal/medial area ratio is at least about 10% in the presence of the agent compared to a control, more usually a decrease of at least about 20%, and may decrease by as much as about 25%, or more.

Anti-restenotic agent. Compounds for use in the present invention inhibit restenosis. While the methods of the invention are not limited by any hypothesis of action, it is believed that restenosis is a natural healing process in response to the arterial injury that occurs during all types of angioplasty procedures. This very complex healing process results in intimal hyperplasia, more specifically migration and proliferation of medial smooth muscle cells (SMC) from the medial to the intimal area of the vessel. The problem associated with this arterial healing process is that in some instances, it does not shut off, and the artery continues to "heal" until it becomes occluded. It should be noted that restenosis is not a re-deposition of the plaque-like cholesterol material that originally occluded the artery.

Prevention of restenosis is tied to an inhibition of SMC proliferation, through release of a pharmacologic agent at the site of injury, e.g. angioplasty. For the purposes of the present invention, the pharmacologic agent is released locally, e.g. through a drug delivery stent positioned at the angioplasty site. The process of restenosis may be initiated shortly after injury to the vessel and may continue for a period of from about 3 to 6 months. Preferably the anti-restenotic agent is released immediately after the prosthesis is secured to the lumen wall to lessen cell proliferation. The drug should then continue to elute for up to about three to six months in total.

Anti-restenotic agents useful in the methods of the invention inhibit restenosis, as defined above. Specific agents shown herein to be anti-restenotic agents include angiotensin converting enzyme inhibitors; nicotine receptor agonists, agents that increase concentrations of nitric oxide, anti-angiogenic agents, agonists of the TGF-beta receptor; death domain receptor ligands; and thrombin inhibitors. The agents may be delivered in the form of polypeptides, peptides, small organic molecules, nucleic acids encoding a polypeptide of interest, and the like. A polypeptide may be any translation product of a nucleic acid regardless of size and glycosylation. Agents may also be in the form of simple drugs, peptides, peptide fragments, DNA, RNA, ribozymes or engineered hybrids of nucleic acids and peptides or peptide fragments, or derivatives of each.

Angiotensin converting enzyme inhibitors (ACE-I) are used for antihypertensive and renoprotective actions. ACE inhibitor include, but are not limited to, captopril, benazepril, enalapril, fosinopril, lisinopril, quinapril, Ramipril, imidapril, perindopril, erbumine, and trandolapril. ACE receptor blockers may also be used in place of or as well as ACE inhibitors, and these include losartan, irbesartan, candesartan, cilexetil, and valsartan.

Nicotine receptor agonist, e.g. nicotine (S-3-(1-methyl-2-pyrrolidinyl)pyridine) and other compounds that substantially specifically bind a nicotine receptor and provide a pharmacological effect. "Nicotine receptor agonists" encompass naturally-occurring compounds (including, but not-limited to, small molecules, polypeptides, peptides, etc., particularly naturally-occurring plant alkaloids, and the like), endogenous ligands (e.g., purified from a natural source, recombinantly produced, or synthetic, and further including derivatives and variants of such endogenous ligands), and synthetically produced compounds (e.g., small-molecules, peptides, etc.) The term "nicotine" further includes any pharmacologically acceptable derivative or metabolite of nicotine which: exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof.

Agents that increase nitric oxide are of interest as anti-restonic agents, e.g. S-nitrosopenicillamine, sodium nitroprusside, N-ethyl-2-(1-ethyl-2-hydroxy-2-nitrosohydrazino) ethanamine (NOC 12), etc. The production of nitric oxide may also be modulated by cytokines, such as γ-interferon, tumor necrosis factor, IL-1, IL-2 and endotoxin due to their effect on the enzyme, nitric oxide synthase. The inducible form of NO synthase is increased by cytokines and the constitutive form seems to be decreased by cytokines. HMG-CoA reductase inhibitors have been found to upregulate endothelial cell NOS activity, as described by U.S. Pat. No. 6,147,109, Liao et al. Any of the forms of nitric oxide synthase can be utilized, as the protein or an active fragment derived therefrom, or as a DNA construct for expression.

Also of interest for the inhibition of restenosis are compounds with an anti-angiogenic effect. These include the anti-angiogenic polypeptides: angiostatin (O'Reilly et al. (1994) Cell 79:315–328); endostatin (O'Reilly et al. (1997) Cell 88: 277–285); and anti-angiogenic anti-thrombin III (Bock et al. (1982) Nucleic Acids Res. 10 (24), 8113–8125); and the like, and further include functionally active variants and derivatives thereof. Other anti-angiogenic agents include inhibitors of matrix metalloproteases, e.g. amifostine, WR-1065; marimastat, primomastat, alpha-1 antitrypsin; sphingosine and the like.

Alternatively, compounds that block thrombin, and other anti-coagulants, may be used to inhibit restenosis, such compounds based on the tripeptide motif D-Phe-Pro-Arg; e.g. LY287045, etc. Many compounds, such as inogatran and melagatran, are known in the art. For non-limiting examples, see U.S. Pat. Nos. 6,326,386; 6,232,315; 6,201, 006; 6,174,855; 6,060,451; and 5,985,833; among others.

Agonists of the TGF-beta receptor are also of interest. TGF-β receptor Type I and type II mediate most activities of TGF-beta(Ebner et al. (1993) Science 260:1344–1348; and Franzen et al. (1993) Cell 75: 681–692). Ligands include TGF-β, and mimetics and biologically active derivatives thereof. Noncovalent attachment of rapamycin to aestent-based delivery system is also of interest. Noncovalent attachment can consist of hydrogen bonding, van der waals forces, or simply passive entanglement in a highly viscous surface, or some combination thereof. Carriers specific to angiostatin can be applied for tight regulated binding, and cleavable linkers sensitive to moisture (time dependant in vivo), pH, osmolality, or a particular antigen among others are included, as are future linkers and related linkers well known to those skilled in the art.

Covalent or noncovalent attachment of antiplatelet agents are also of interest. Preferred among these are the GPIIb/IIIa inhibitors. Most preferred is RheoPro.

For the induction of apoptosis, agents of interest include death domain receptor ligands, which are compounds, usually polypeptide compounds, that bind to mammalian cell surface receptors comprising a death domain, or homologs or orthologs thereof, and that, by binding so deliver a signal for apoptosis to the cell. The intracellular protein interactions triggered by these receptors can be attributed to binding interactions of the death domain, which is homologous to an approximately 80 amino acid domain near the C-terminus of TNF-R1, and is responsible for signaling cytotoxicity (Huang et al. (1996) Nature 384:372–5). The TNF receptor death domain family includes TNF-R1, Fas (CD95), TRAMP (wsl/Apo-3/DR-3), TRAIL-R1 (DR-4) and TRAIL-R2 (DR-5, TRICK2, KILLER). Death domain ligands include proteins that regulate cellular proliferation and differentiation by binding to specific death domain receptors. These ligands include the TNF family, e.g. TNF, lymphotoxin, CD30 ligand, 4-1 BB ligand, CD40 ligand, CD27 ligand, and TRAIL (TNF-related apoptosis-inducing ligand), and homologs and analogs thereof. The functional, soluble forms of TNF as well as human FasL exists as trimers. Lymphotoxin β, a member of the TNF family, consists of a heterotrimer of one (lymphotoxin-α, or TNF-β) and two β chains (lymphotoxin-β) on the membrane.

Anti-restenotic polypeptides and peptides can be administered in their native form, or through the administration of nucleic acids encoding the molecule of interest. Administration of nucleic acids results in genetic alteration of targeted cells. The nucleic acid materials for delivery to targeted tissue encodes a gene product for which expression is desired, and a promoter for expression of the gene product. By "nucleic acid of interest" is meant any DNA, RNA, ribozyme, hybrid or analog thereof that encodes a polypeptide or other gene product that is desirable for expression in tissue of a subject. The gene product can include a polypeptide, an anti-sense mRNA, or other gene product that is desirably expressed. The term "DNA of interest" or "DNA" is used herein as shorthand to refer to the nucleic acid of interest and is not meant to be limiting. The nucleic acid delivered to the tissue in vivo can take any number of forms. For example, the nucleic acid can be introduced as a linear or circular molecule, preferably a circular molecule (e.g., a circular plasmid or other construct).

The nucleic acid of interest and the promoter are operably linked to provide a construct, or vector for expression. Normally, "construct" will refer to a nucleic acid molecule that facilitates expression of a gene product encoded by the nucleic acid to be introduced. By "operably linked" is meant that a DNA sequence and a regulatory sequence(s) (e.g., a promoter sequence) are connected in such a way as to permit transcription when the appropriate molecules (e.g., transcriptional activator proteins) are bound to the regulatory sequence(s).

The amount of DNA to accomplish expression of an anti-restenotic gene product at an effective level will vary according to the desired effect, as well as with other variables such as the age of the subject, the tissue to be genetically altered, the gene product to be expressed and the desired level of its expression, etc. In general, the amount of DNA administered is an amount sufficient to provide for transformation of a number of cells that in turn provides for a level of gene product expression from the introduced DNA to provide for a desired effect. Dosages are routinely determined in the art, and can be extrapolated from the amounts of DNA effective in an animal mode (e.g., a rodent (mouse or rat) or other mammalian animal model), in which factors such as the efficiency of transformation and the levels of gene product expression achieved can be readily assessed and extrapolated to other vertebrate subjects.

The nucleic acid of interest can be obtained from any of a variety of sources or methods well known in the art, e.g. isolated from suitable cells, produced using synthetic techniques, etc., and the constructs prepared using recombinant techniques well known in the art. Likewise, techniques for obtaining expression of DNA or RNA sequences in a genetically altered host cell are known in the art (see, for example, Kormal et al., Proc. Natl. Acad. Sci. USA, 84:2150–2154, 1987; Sambrook et al. Molecular Cloning: A Laboratory Manual, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Expression of the introduced nucleic acid can be short-term, i.e. a few hours to several hours to a few days, or permanent or long-term i.e. from a week to several weeks to a few months or more. In general, gene product expression from the introduced nucleic acid ranges from at least about 1 to 2 days, or 3 to 5 days, to about 1 week, generally about 1 to 4 weeks, up to about 6 weeks, and may be-as long as about 10 to 12 weeks or longer. Where expression times of more than a few weeks are desired, for example from about 10 to 12 weeks or longer, expression of the gene product can be maintained by using a retroviral construct having inactivated LTRs and an internal promoter in the construct to drive gene product expression.

Complex systems of drugs may be carried by the prosthesis. An anticoagulant or antiplatelet may be included in the outermost surface of the device in order to elute off very quickly for the first several days. Antiinflammatories and antireplicates can be formulated into the device to continue to elute later, when in contact with non-blood cells after neointima overgrowth has surrounded the device. The drug elution rate does not need to be uniform, and may be tailored to fit the need of the patient.

Targeted Drug Delivery. The anti-restenosis agents are delivered to a targeted site in the vessel, usually the site of an injury, such as angioplasty, where it is expected that neointimal hyperplasia will occur. A useful device for such delivery is a stent modified for drug delivery, where the term stent is used as is known in the art, to refer to a prosthesis which can be inserted and held, when desired, in a lumen of a blood vessel for the treatment of restenosis, e.g. following angioplasty. Methods of particular interest provide for release of the anti-restenotic agents to inhibit in-stent restenosis.

Figure 1A:
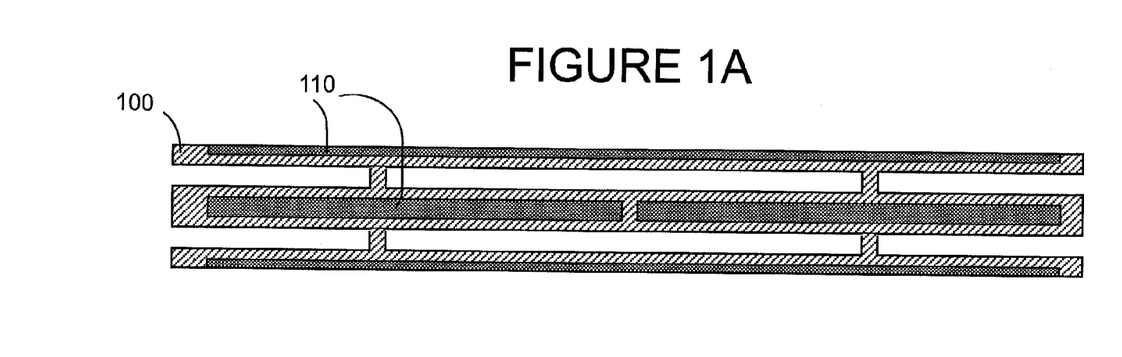
FIG. 1A is a diagram of a channeled stent.
Figure 1B:
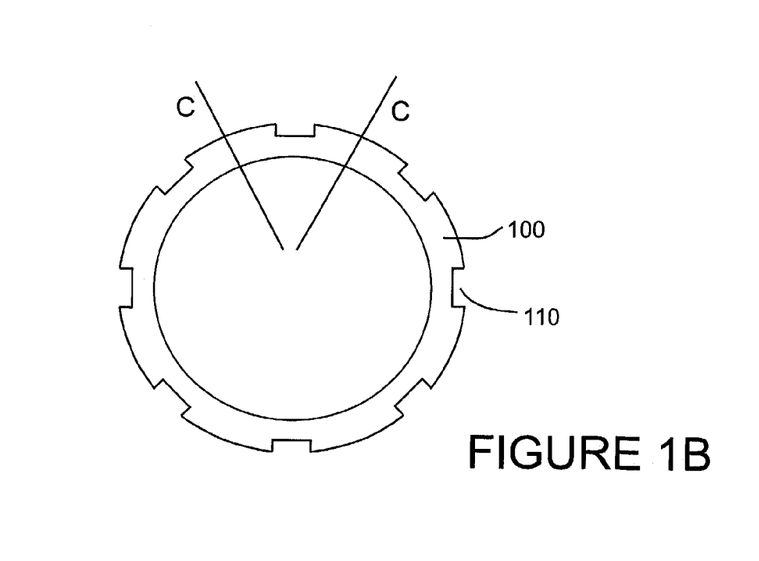
FIG. 1B is a cross-sectional view of the stent and channels.

A number of stents have been described for the targeted release of biologically active agents. A drug delivery platform of particular interest is described in co-pending patent application Ser. No. 10/101,455, which claims priority to provisional application 60/285,383, both herein incorporated by reference. This drug delivery platform utilizes a stent 100, as shown in FIGS. 1A and 1B, which comprises channels 110 on the surface, which may be on either or both of the abluminal (toward the wall) or adluminal (toward the lumen) surfaces. Contained within the channels is a matrix 130 comprising a biologically active agent; the stent being ensheathed in a gel covalently bound to the stent surface which may be derivatized 120 for that purpose, where the gel is optionally also bound to the matrix. The stent may be formed of any suitable material, including biologically compatible metals, shape memory plastics, biodegradable or bioerodible polymers, and the like.

Channel dimensions and architecture are designed to achieve the desired percent coverage and delivery location while preserving mechanical integrity. The dimensions of the channels are dictated by the requirements for the specific use, and are sufficient to contain the unit size of the matrix, e.g. microspheres of 1 to 50 μm diameter, and of a depth not so great that it compromises the integrity of the stent's structure. The depth will usually be at least about 10 μm, more usually at least about 20 μm, usually not more than about 200 μm, more usually not more than: about 100 μm, and preferably are about 45 to 65 μm in depth. The depth is usually greater than about 10% of the total depth of the stent structure, usually greater than about 50% of the total depth of the stent structure, usually not more than about 80% of the total depth of the stent structure.

The length of the channel may be up to and including the length of the stent, or where the stent has a strut pattern, along the entire circumference, or a fraction thereof. The width of the channel is sufficient to contain the unit size of the matrix and still maintain the structural integrity of the stent. For example, the channels are usually at least about 10 μm in width, more usually at least about 20 μm in width, preferably at least about 45 μm in width, where the upper boundary of width is determined by the specific stent design, but is generally not more than about 50 to 75% of the total width of the element, i.e. strut, tube, etc.

Channels may be tapered in cross-section, such that the width at the stent surface is wider than the width at the bottom of the channel, e.g. a V shape, a U shape, a V shape with a flat bottom, etc. Where the channel is tapered, at the stent surface, the tapered channel is usually more than about 10% of the strut width, usually more than about 50 or more than about 75% of the surface width, and may be as much as 100% of the surface width. Depth for tapered channels are as described above for a non-tapered channel. The degree of taper will determine the width of the channel at the bottom, where a V-shaped taper will result in a width of about 0 to about 10% of the width of the stent structure. A broader bottom may also find use, where the width of the channel at the bottom will be from about 10% to about 50% of the width of the stent.

The stent surface may be derivatized for covalent binding of a highly viscous agent or component of a gel-forming composition, which can be applied in the absence or presence of channels described above. The use of silane coupling reagents, especially those of the formula R'Si(OR)$_3$ in which R' is typically an aliphatic group with a terminal amine and R is a lower alkyl or chloro group, to attach a macromolecule or polymer covalently to a solid support is well known in the art. Organosilanes include 3-methacryloxypropyltrimethoxysilane; aminopropyltriethoxysilane ; (APTES); 3-mercaptopropyltriethoxysilane (MPS); glycidoxypropyltriethoxysilane (GOPS), and the like.

A biodegradable, bioerodible or biocompatible non-biodegradable matrix comprising the anti-restenotic agent is bound to the channels of the stent surface. The matrix may be of any geometry including fibers, sheets, films, microspheres, circular discs, plaques and the like. Microspheres are usually at least about 5 μm in diameter, more usually at least about 10 μm in diameter, and are usually not more than about 100 μm in diameter, more usually not more than about 50 μm in diameter. Some examples of biodegradable polymers useful in the present invention include hydroxyaliphatic carboxylic acids, either homo- or copolymers, such as polylactic acid, polyglycolic acid, polylactic glycolic acid; polysaccharides, celluloses, acrylate polymers, and the like. The matrix may be covalently bound to the gel.

Various techniques known in the art may be employed to entrap the anti-restenotic agent in the matrix. Useful techniques include solvent evaporation methods, phase separation methods, double emulsions methods, UV crosslinking, chemical crosslinking, self-assembling systems based upon covalent or noncovalent interactions, interfacial methods, extrusion methods, molding methods, injection molding methods, heat press methods and the like. The ratio of agent to polymer will vary with the desired rate of release, the amount of agent generally varying in the range of 1 to 80 weight percent of the polymer in addition to other agents present. The ratio of drug to polymer may be adjusted to produce optimized compositions.

The gel is selected to be a polymeric compound that will fill the spaces between the matrix and the channel, that can be covalently bound to the stent surface and optionally covalently bound to the matrix, and that provides a porous protective barrier between the matrix and the environment, for example during storage, implantation, flow conditions, etc. The gel may contribute to the control of drug release through its characteristics of degradation and diffusion. In additional, the gel may comprise a biologically active agent that is the same or different from the biologically active agent present in the matrix.

Other devices may be used for targeted drug delivery. In one embodiment of the invention, the anti-restenotic agent is formulated as a liquid for release from a stent. For example, a stent may include a chamber with a drug transport wall, where the anti-restenotic agent is loaded into the chamber, then selectively transported through the wall (see U.S. Pat. No. 5,498,238). Other variations of this approach include the use of a hollow tubular wire stent, or a stent comprising a reservoir. Such stents are described in the art as having side walls facing outwardly having holes for delivery of the liquid formulation to the targeted site, where the stent is implanted (U.S. Pat. No. 5,891,108). The anti-restenotic agent may be diffused from a reservoir directly to the walls of a blood vessel, through directional delivery openings arranged on an outer surface of the stent. Such devices may also comprise an osmotic engine assembly for controlling the delivery of the agent from the reservoir (U.S. Pat. No. 6,071,305).

An alternative to liquid formulation is provided by stents that comprisea drug compounded to the device itself. In one embodiment, the stent itself is formed of a polymeric material comprising the anti-restenotic agent, where the stent is biodegradable or bioabsorbable (see U.S. Pat. No. 6,004,346). Alternatively, the prostheses may be biostable in which case the drug is diffused out from the biostable materials in which it is incorporated. With metal stents, the device can include a drug-carrying coating overlying at least a portion of the metal.

Other devices have been described that include a drug carrying coating, which may be used in the methods of the invention. For example a porous stent can be made from a powdered metal or polymer, where the anti-restenotic agents are then compressed into the pores of the stent (see U.S. Pat. Nos. 5,972,027; and 6,273,913). Stents for drug delivery can also comprise multiple coatings, where the rate of release is different for the two coatings (see U.S. Pat. No. 6,258,121), where one of the anti-restenotic agents can be present in both coatings to provide for an extended release profile; or where two or more anti-restenotic agents are differentially released. Other composite coatings include at least one composite layer of the anti-restenotic agent and a polymer material, and at least a barrier layer positioned over the composite layer and being of thickness adequate to provide a controlled release of the bioactive agent (see U.S. Pat. No. 6,335,029). The sheath over the coating containing the anti-restenotic agent can also be perforated, so that when the stent is compressed, the perforation is closed. Upon placement in the vessel, the stent is expanded, and the perforation is opened (see U.S. Pat. No. 6,280,411).

METHODS OF USE

The anti-restenotic agents and targeted drug delivery device are useful any vascular surgery, such as may be used in any situation in which the flow of blood through a vessel has been compromised. There are a variety of conditions where there is restricted blood flow through that vessel. Occlusive vascular conditions of interest include atherosclerosis, graft coronary vascular disease after transplantation, vein graft stenosis, peri-anastomatic prosthetic graft stenosis, restenosis after angioplasty, coronary artery disease, peripheral vascular disease or other forms of occlusive arterial disease, and the like. The prevention of in-stent restenosis is of particular interest.

In a complex biological process such as restenosis, a therapeutic strategy may involve multiple therapeutic factors, e.g. released with multiple time courses. Strategies may utilize combinations of microspheres or other drug formulations and gels containing different agents and/or that are formulated for different release profiles. Due to their versatility, the controlled release materials can be adapted and combined to provide the desired time course and dose-response for each stent and application.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

EXAMPLE 1

Stent-Based Local Delivery Platform

Stent design and loading. The stent design for this initial example is based on the Palmaz-Schatz coronary stent. The stainless steel stent is 1.6 mm in diameter and 10 mm in length and has 10 longitudinal struts evenly spaced circumferentially, and it is designed to be balloon expandable up to 5 mm diameter. Its basic slotted tube design was modified by electro-discharge machining (EDM) channels 80 microns wide by 60 microns deep along the length of the abluminal (toward the wall) side of each strut. The stent is designed to provide abluminal (toward the wall) but not adluminal (toward the lumen) delivery. With these dimensions, the channels cover 8.5% of the lumen wall area when deployed to a nominal diameter of 3 mm. The channels were machined from end to end in order to allow drug delivery both to the wall and to the tissue surrounding the stent end which both represent critical sights for neointima formation. Microspheres, which can hold and release therapeutic agents (for example, see Yuksel et al. (2000) *Plast Reconstr Surg.* 105(5):1721–9; Waugh et al. (1999) *Circ Res.* 84(1):84–92 were mechanically loaded into these channels. Excess microspheres were removed with a needle and short bursts of air from a compressed air canister.

Figure 1C:
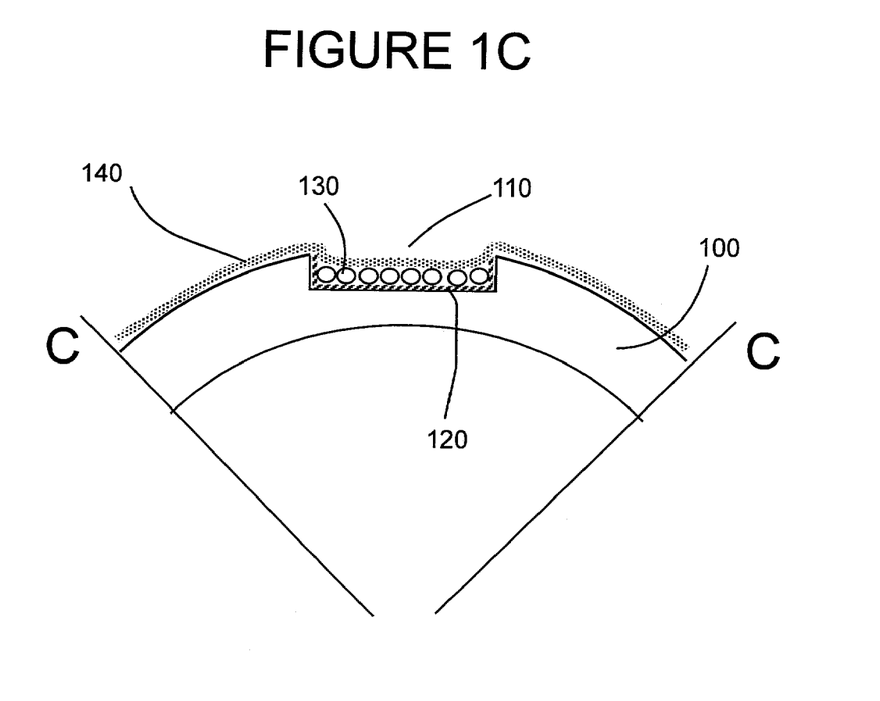
FIG. 1C is a close-up view of the stent.

The corresponding design and post-manufacture stent appear as FIGS. 1A to 1C. No mechanical failures occurred during the deployment of over 60 stents of this design. Stent channels were filled by manual loading with PLGA (75:25)-PEG-buffer microspheres with a mean diameter of 50 μm. Predetermination of microsphere size can be difficult for certain drug-loads, and smaller microspheres are more readily loaded. As a result, quantitative evaluation of stent filling as percent of total channel was subsequently evaluated for both large and small microspheres.

Microsphere preparation. Bioerodible polyethylene glycol-polylactide-co-glycolide (PLGA, Polysciences, Warrington, Pa.) microspheres (MS) were prepared as a modification of previously described techniques (Yuksel, et al., supra.) A mixture of 8:1::PLGA (75:25):PEG-8000 (polyethylene glycol, MW 8000, Sigma, St Louis, Mo.) was employed with the double emulsion technique to generate microspheres (MS) of final diameter 50 or 10 μm. Additionally, a pH buffer of 7.4 was incorporated in all MS preparations as a modification of other techniques to limit local pH changes (Zhu et al. (2000) *Nature Biotechnology* 18:52–7. Separately, MS containing PEG-dimethacrylate instead of PEG were also prepared to a final size of 10 μm.

In vitro flow retention and channel fill density determination. To evaluate whether flow over the surface of the loaded stents resulted in dislodging of MS, stents were advanced into in vitro flow. Loaded MS-stents were mounted on a 4.0 mm×2.0 cm noncompliant balloon. Two 25–30 cm segments of Tygon tubing were joined with a 5 cm segment of shrink tubing. Phosphate buffered saline (PBS) was introduced and adjusted to a flow rate of 250 ml/min. The stent was introduced from the downstream end of the tubing and advanced to the center of the shrink-tubing segment and maintained for a total of 2.0 minutes. The stent was withdrawn and employed for fill density analysis.

To determine the mean percent of each channel that was filled with MS, the entire length of each channel was photographed with single composite photographs of each generated and employed in ImagePro Image analysis suite.

Stents were examined on a Nikon E600 microscope with plan apochromat lenses at a total magnification of 40×. High resolution digital images were acquired using a Diagnostic Instruments true color SPOT camera. The entire length of each channel was photographed with single composite photographs of each generated and employed in ImagePro image analysis suite to determine the mean percent of total channel filled with MS.

Stents were manually loaded with microspheres of mean diameter 50 μm (b-MS) or 10 μm (s-MS), loaded onto a balloon, and the entire length of each stent channel was photographed. Mean channel fill density was calculated as the percent of total channel filled with microspheres. Stents were subsequently introduced into a flow loop in vitro in a transparent segment of tubing. The entire length of each stent channel was again photographed and analyzed. No statistically significant decrease in b-MS loading occurred after introduction to flow (P=0.3351), while s-MS encountered significant loss of microspheres in flow conditions (P=0.0001). However, certain drug/microsphere preparations necessitate smaller sizes due to concentration, molecular charge and volume requirements. In addition, smaller sizes are desirable to ease manual loading or automate loading. Given that some drug loads may necessitate small final MS sizes and small MS offer some technical advantages for stent-loading, strategies for hybrid systems to increase s-MS retention were subsequently investigated.

Hybrid strategies for retention in vitro and in vivo—gel preparation and stent loading. Stents were either rinsed with saline or pretreated with 2% 3-methacryloxypropyltrimethoxysilane (meac) in 75% ethanol and heat cured for 60 minutes at 105° C. (silane-stents employed where described). The s-MS (either meac-MS or MS) were loaded as before and loaded stents were ensheathed in silicone tubing. One set of stents was loaded with 30% pluronic F-127 at a temperature of 4 C. For other groups, a 20% mixture of 3:2::PEG-dimethacrylate:PEG with 900 ppm photoinitiator (HMPP) was introduced to fill unoccupied spaces within the channels. Ensheathed stents were exposed to UV-A overnight. Silicone tubing was withdrawn. Stents were loaded on 4.0 mm×2.0 cm noncompliant balloons and lyophilized overnight prior to use.

To evaluate whether in vivo advancement and deployment altered MS density, adult male New Zealand White rabbits weighing 3.8–4.2 kg underwent general anesthesia induced with ketamine/medetomidine and maintained with isoflurane. An arteriotomy was performed and a 5F introduction sheath was placed. Under fluoroscopic guidance using a Siemans Angiostar, aseptically prepared stents were deployed in the infra-renal abdominal aorta. Pre- and post-deployment digital subtraction-angiograms were recorded for each. Stents were post-dilated with a 5 mm angioplasty balloon,(Jupiter, Cordis, Miami, Fla.) to a-final lumen size of 125% of baseline with care taken to ensure that no branches were present within 5 mm of either end or within the stent segment. Post-deployment angiograms were also recorded for each. Animals employed for channel fill density analysis underwent total-body perfusion-fixation under anesthesia with immediate excision of the aortic segment containing the stent. Stents were photographed for channel fill density as above both through the aortic wall and after excision from the aortic segment. Animals undergoing plaque evaluation and inflammatory infiltrate analyses were recovered and maintained for 7 days prior to total-body perfusion fixation as previously described. Treated segments were harvested, stents carefully excised and segments post-fixed in neutral buffered formalin (NBF) for 12–14 hrs. Specimens were paraffin embedded and employed for plaque analysis or evaluation of local inflammatory infiltrate as described.

Stents containing s-MS were again prepared as above and ensheathed en toto in silicone tubing. The spaces around the MS within each channel were filled with a rapid-release gel formulation in an attempt to prevent loss of s-MS under flow conditions. The entire length of each stent channel was again photographed and mean channel fill density calculated. These stents (MS/plu) were subsequently introduced into an in vitro flow loop, and channel fill density was calculated after flow exposure. Finally, MS/plu stents were introduced into the rabbit common femoral artery, advanced and deployed in the infrarenal abdominal aorta. The aortic segments were subsequently excised and mean channel fill density after in vivo deployment was calculated both through the nearly transparent aortic wall (results not depicted) and after stent removal. Stent removal did not result in significant change in fill density. Gel loading results in minimal loss of fill density, but exposure to flow again results in substantial loss of s-MS from the stent (P=0.0001). In vivo deployment encounters still worse retention rates (P=0.0201).

New stents were pretreated to form a metal oxide-methoxysilane-monomethacrylate link to the metal-oxide layer of the stent surface. Silane stents were then loaded with either s-MS containing PEG-dimethacrylate or s-MS with PEG as above. Stents were ensheathed and a 20% mixture of 3:2:: PEG-dimethacrylate:PEG was introduced to fill unoccupied spaces within the channels. Gels were subsequently polymerized to form gel-stent links (MS-gel) or gel-stent-microsphere links (MS-meac-gel). Stent channel fill density was again evaluated after balloon loading, after in vitro flow loop exposure-and after in vivo deployment in rabbit aortas. Significant improvements in s-MS retention occurred for MS-gel in vivo relative to MS-plu (P=0.0001) and in vitro under flow conditions (P=0.0001 vs. MS-plu, P=0.0001 vs. s-MS). Most importantly, no significant loss occurred when MS-gel groups were subjected to flow conditions (P=0.3336) or in vivo deployment (P=0.4244). While MS-meac-gel had statistically significant improvements in MS retention in vitro and in vivo. relative to MS-plu (P=0.0010, P=0.0001 respectively) and s-MS (P=0.0001 in vitro), these meac-s-MS particles were far less efficiently loaded than with s-MS without methacrylate. Additionally, MS-meac-gel exhibited significant loss of MS after in vivo deployment (P=0.0004) while MS-gel did not. Thus, MS-gel exhibited the best performance under all conditions. Additionally, no mechanical failures (fractures, perforations, etc.) or complications occurred in any group, including MS-gel. Immediately post-deployment there is distal spasm but no luminal compromise, perforation, or failure. By the time of harvest, the lumen remains patent, the stent intact, and no complications are present.

In summary, a solution for hybrid MS-retention is a gel that protects the microspheres from embolization during advancement and deployment. A crosslinked PEG-methacrylate gel was subsequently investigated. Initial experiments revealed that channel contents separated from the stent readily but did not fragment from one another. The stent channels were subsequently modified to add a methacrylate link to the metal-oxide layer of the stent in order to enhance channel retention of the polymers. Small microspheres were either prepared as before or modified to contain PEG-methacrylate. Gel polymerization thus anchored the gel to the channel and, in the latter group, to the surface of the microspheres themselves. Retention rates for this gel system were virtually complete under flow and after in vivo deployment. Thus, a stent system potentially allowing controlled drug delivery without embolization of polymers was developed. Given the progressive loss of methacrylate MS when exposed to flow and in vivo deployment and the relative ease of loading s-MS without methacrylate, subsequent experiments incorporated s-MS without methacrylate.

Local inflammation. To evaluate whether the stent platform altered local inflammatory infiltrate, paired sections from the 7 day timepoint above were employed for granulocyte determination using chloroacetate esterase staining or for macrophage evaluation using immunohistochemistry (RAM-11, DAKO, Carpinteria, Calif.) as previously described by Waugh, et al. (2000). Circulation 102:332–337. Number of granulocytes and macrophages was determined for each cross section, with mean and standard error tabulated by group.

Since certain polymer systems have been shown to lead to local inflammation, cross-sectional macrophage and neutrophil infiltrate were examined for each group. Results are detailed in Table 1. No statistically significant differences in local macrophage or neutrophil infiltration occurred in MS-gel vs. Palmaz-Schatz stents (P-S) (P>0.05 for each comparison).

TABLE 1

Inflammation after stent implantation in vivo.

| | Neutrophilic Granulocytes | Macrophages |
|---|---|---|
| P-S | 96.1 ± 8.9 | 0.267 ± 0.153 |
| MS-gel | 90.0 ± 8.8 | 0.133 ± 0.091 |

Number of granulocyte esterase positive (neutrophilic granulocytes) or RAM-11 positive (macrophages) cells per cross section (mean ± SE).

Plaque evaluation. To evaluate whether the stent platform itself worsened plaque formation and whether the system could detect any therapeutic effect, animals (n=5 per group) underwent stent implantation with normal (unchanneled) commercially available Palmaz-Schatz stents of identical dimensions, channel stents containing s-MS/PEG gel as prepared above (without any therapeutic factor), or channel stents loaded with s-MS/PEG gel containing a nitric oxide donor as an antineointimal agent. The NO-nucleophile complex in this study, N-Ethyl-2-(1-ethyl-2-hydroxy-2-nitrosohydrazino) ethanamine (NOC-1 2, Calbiochem, San Diego, Calif.), releases two equivalents of NO per NOC-12. Animals were recovered and maintained on 0.25% cholesterol chow. On day 7, treated segments were excised and processed as described and cross sections employed for Verhoff elastica-Masson trichrome double staining as previously described (Waugh et al., supra.) Photographs of each aorta were acquired as before. Ratio of intima to media for each cross section was determined from the appropriate area measurements, with mean and standard error tabulated for each group.

Figure 2:
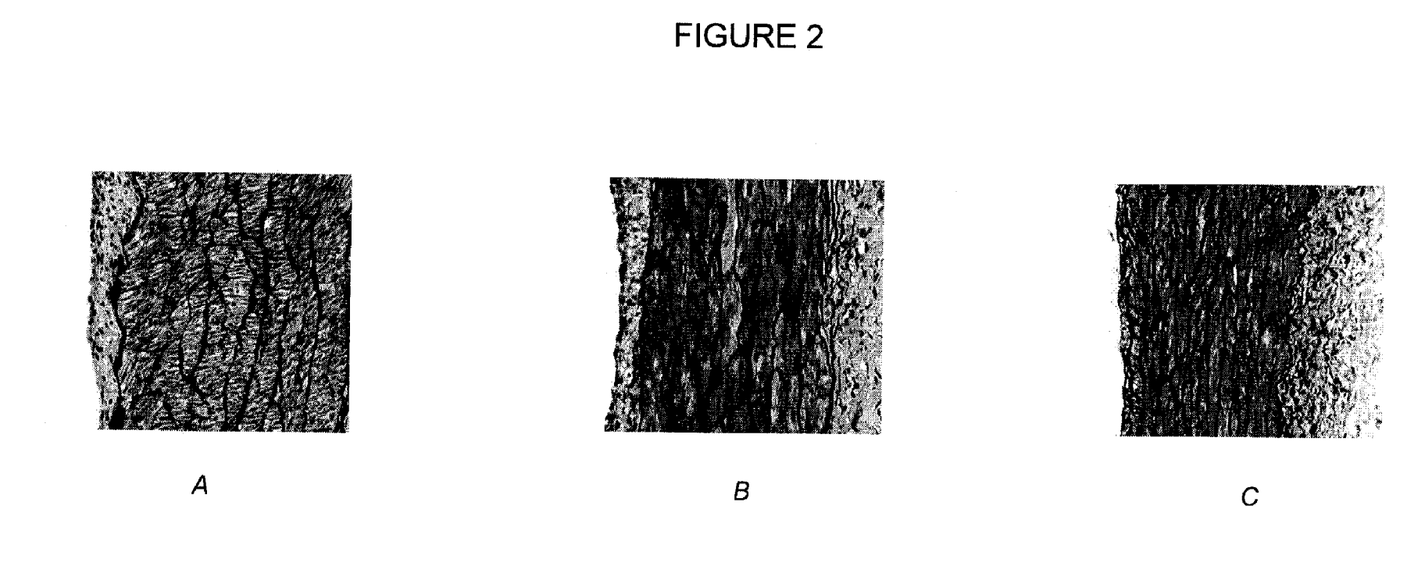

The impact of MS-gel stents on in-stent restenosis was subsequently evaluated, along with the suitability of this system to evaluate anti-restenotic agents. Briefly, animals underwent implantation of normal P-S stents, MS-gel stents containing polymer only (MS-gel), or MS-gel stents containing a therapeutic level of a nitric oxide donor as an anti-restenotic agent (MS-gel-NO). Early plaque formation was evaluated after 7 days through intima to media ratios to evaluate whether stent design or therapeutic factor altered early in-stent restenosis in a critical window. The results are summarized in FIGS. 2A–2C. As indicated, MS-gel stents did not encounter significantly altered rates of early in-stent restenosis relative to P-S controls (P=0.1126). In contrast, MS-gel-NO stents reveal a significant reduction in early plaque reduction relative to both controls (P=0.0001 vs. P-S, and P=0.0001 vs. MS-gel).

Given that polymer systems prepared differently than those employed here have encountered high rates of inflammation and may adversely impact plaque formation, in vivo deployment of this stent system was evaluated relative to deployment of commercially available Palmaz-Schatz stents. The polymer-loaded stents encountered comparable rates of local macrophage and neutrophilic granulocyte infiltration after seven days relative to Palmaz-Schatz stents as detailed above. Perhaps more importantly, no statistically significant alteration in rates of in-stent plaque formation was evident relative to conventional stents of comparable dimensions. Thus, these polymer-loaded stents do not appreciably worsen the system which they were designed to evaluate and treat. These results are in sharp contrast to recent reports of polymer-only systems which require cytotoxic agents to avert increases in inflammation and plaque progression relative to conventional stents (Tamai et al. (2000) Circulation 102:399–404; van der Giessen et al. (1996) Circulation 94:1690–1697; Colombo and Karvouni (2000) Circulation 102(4):371). Given the technical, mechanical and biologic disadvantages of alternative local release strategies, no prior evaluation of potential anti-restenotic local agents has been effectively undertaken. The present platform thus represents an important and necessary step in the development of effective strategies for in-stent restenosis and management of cardiovascular disease.

We subsequently evaluated whether the present system was sensitive enough to detect therapeutic levels of an anti-restenotic agent of any nature. Here, in vivo deployment of this system with one such agent, a nitric oxide donor, resulted in substantial declines in plaque formation relative to both polymer-loaded stent controls and conventional Palmaz-Schatz stents alone. Thus, this system has proven to be a relatively nonperturbing, effective, and sensitive method for evaluation and therapeutic delivery of putative anti-restenotic agents. Previously, identification of drugs locally effective in preventing in-stent restenosis has proven difficult, due to lack of a simple controlled release platform.

With the present platform, selection and optimization of agents to locally prevent in-stent restenosis can now be readily accomplished. Although demonstrated here in a variation of a Palmaz-Schatz stent for simplicity, the present strategy can be translated to virtually any stent design type.

Alternative stent designs. The strategies for local drug delivery described above are applied to other mechanical stent designs and can be accomplished with other machining techniques. For example, using laser machining techniques similar to those currently employed to manufacture modern stents, channels were cut into the abluminal surface of a BX-Velocity stent (Cordis Corporation, Miami, Fla.). The channels shown are approximately 75 microns in width and 60 microns deep and follow the strut pattern faithfully around the entire stent circumference. Channeled BX-Velocity stents have been treated successfully with the s-MS/PEG gel preparation.

EXAMPLE 2

Stent-Based Release of an Angiogenesis Inhibitor Limits In-stent Plaque Progression Microsphere Preparation. Biodegradable poly(lactic-co-glycolic-acid)-polyethylene glycol (PLGA/PEG) microspheres were prepared as a modification of previously described techniques. A mixture of 8:1::PLGA(75:25):PEG-8000 was employed with the double emulsion technique to generate a final microsphere diameter of 10 microns, and a degradation time of approximately 4 weeks. Additionally, a pH buffer of 7.4 was incorporated to limit local pH changes in order to stabilize incorporated drugs and render the microspheres more biocompatible. During the microsphere manufacturing process, 2.0 mg of the angiogenesis inhibitor angiostatin (Calbiochem, La Jolla, Calif.) in 200 ml phosphate buffered saline was added to the polymer solution. Control microspheres (blank microspheres) containing polymer and buffer without any drug were also prepared. Stents were prepared as above.

In Vivo Stent Implantation. Age-matched adult male New Zealand White rabbits weighing 3.8–4.2 kg were used in accordance to NIH and institutional guidelines (n=6 animals per group). Under general anesthesia, an arteriotomy at the femoral artery was performed and a 5 Fr introducing sheath was placed. Under fluoroscopic guidance, aseptically prepared channeled stents filled with blank or angiostatin microspheres were deployed in the infra-renal abdominal aorta. Stents were post-dilated at 8 atm with a 5 mm angioplasty balloon (Jupiter, Cordis, Miami, Fla.) to a final lumen size of 125% above the baseline with care taken to ensure that angiostatin branches were present within the stent segment. Pre- and post-deployment digital subtraction angiograms were recorded for the blank procedural control and angiostatin treatment groups. The rabbits were fed a 0.25% cholesterol diet after the intervention. Early 7 day follow up (n=3 per group) or late 28 day follow-up (n=3 per group) animals underwent total-body perfusion-fixation as previously described with immediate excision of the aortic segment containing stent. The 7 day aortic specimens were excised longitudinally and stents were removed. The resulting aortic segments were divided into two equal subsegments. One subsegment of each underwent fixation in 10% neutral buffered formalin and embedded in paraffin-for light microscopic and morphologic analysis. The remaining subsegment of each specimen was snap frozen for molecular assay. The 28 days aortic specimens were fixed in 10% neutral buffered formalin and were embedded in PolyBed (Polysciences, Warrington, Pa.) for light microscopic and morphologic analysis.

Morphological Analysis of Intima/Media (I/M) Ratios. The seven day analysis consisted of thick (5 µm) cross sections of the aortic wall were obtained from the paraffin-embedded specimens (n=9 sections per group). An elastic von Gieson-Masson trichrome or Elastica van Gieson-Hematoxylin double stain was performed for light microscopic analysis. For the 28 day specimen analysis (n=3 animals per group), each plastic-embedded aorta with stents was cut into five pieces longitudinally equal lengths. These pieces were stained by modified Verhoff elastic staining. Five cross sectional images of the stained aorta were obtained (n=15 sections per group) from one side of plastic pieces. High resolution digital images of histological cross sections were acquired at 100× magnification from a Diagnostic Instruments SPOT true-color camera (Diagnostic Instruments, Sterling Heights, Mich.) as displayed on a Nikon E600 with Plan Apochromat Lenses (Nikon). Using Image Pro Plus software (Media Cybernetics, Silver Spring, Md.), the cross-sectional area of the intima and the media were determined by blinded observers. The ratio of intima area to media area subsequently tabulated for each, with the results presented as Table 2. Mean, standard error, and significance were determined.

TABLE 2

Plaque formation after in vivo stent implantation and angiostatin release.

| | Intima to media ratio |
|---|---|
| Control | 1.981 ± 0.080 |
| Angiostatin | 1.610 ± 0.050 * |

Ratio of intimal area to medial area 28 days after stent implantation for control stents or stents releasing angiostatin (mean ± SE), * denotes P = 0.003 vs. controls.

Evaluation of Local Plaque Stability Parameters: Macrophage Infiltrate and Endothelial Density. Cross sections at the 7 day time point evaluated above were obtained (two per segment) from each vessel and incubated with a primary monoclonal antibody to rabbit macrophage (clone RAM-11, 1/800 dilution, DAKO, Carpinteria, Calif.). The number of positive cells per cross section was counted by a blinded observer. Endothelial cells were stained with CD-31 in order to evaluate endothelial cell density. Mean and standard error were tabulated for each group with significance determined as before and p values as reported. The results of both analyses are presented as Table 3.

TABLE 3

Plaque stability after in vivo stent implantation and angiostatin release.

| | Macrophages | CD31 |
|---|---|---|
| Control | 55.200 ± 3.837 | 4.889 ± 0.696 |
| Angiostatin | 34.889 ± 3.948 * P = 0.0011 | 0.111 ± 0.111 * |

Number of cross-sectional macrophages or plaque microvessels (CD31) 7 days after stent implantation for control stents or stents releasing angiostatin (mean ± SE), * denotes P < 0.05 vs. controls.

Conclusions. Stent based local release of an angiogenesis inhibitor reduces plaque progression after stenting and stabilizes the plaque that does form so that plaque rupture, occlusion, and adverse long-term outcome are reduced in frequency. This strategy works in any stent design for local release of the agent. Polymers, grooved stents, and anchoring are not necessary to achieve these effects, but are presented here for simplicity. The same effects is accomplished via any stent-based local release strategy, and while this example presents use of angiostatin as a specific agent, any anti-angiogenic factor could be substituted with comparable result (i.e. the example demonstrates efficacy of the class of agents).

EXAMPLE 3

Stent-Based Release of a Factor to Increase Nitric Oxide Levels Can Limit In-stent Plaque Progression microsphere/stent preparation. Microspheres were prepared as above (example 2b) except loaded with 40 mg NOC-12 (Calbiochem, La Jolla, Calif.) in 200 µl phosphate buffered saline in place of angiostatin and stents were loaded as before.

plaque formation. Plaque morphometry was assessed as in Example 2, with results summarized as Table 4.

TABLE 4

Plaque formation after in vivo stent implantation and nitric oxide release.

| | Intima to media ratio |
|---|---|
| Control | 1.981 ± 0.080 |
| NO | 1.338 ± 0.051 * |

Ratio of intimal area to medial area 28 days after stent implantation for control stents or stents releasing a nitric oxide donor (NO), (mean ± SE), * denotes P = 0.0001 vs. controls.

Conclusions. Stent based local release of a nitric oxide donor reduces plaque progression after stenting. This strategy works in any stent design for local release of the agent. Polymers, grooved stents, and anchoring are not necessary to achieve these effects, but are presented here for simplicity. The same effects is accomplished via any stent-based local release strategy and while this example presents use of NOC-12 as a specific agent, any NO donor could be substituted with comparable result (i.e. the example demonstrates efficacy of the class of agents).

EXAMPLE 4

Stent-Based Release of an Elastase (or Matrix Metalloproteinase) Inhibitor Can Limit In-stent Plaque Progression.

Local prevention of post-stenting extracellular matrix remodeling can limit plaque progression microsphere/stent preparation. Microspheres were prepared as above (Example 2) except loaded with 40 mg of the elastase inhibitor alpha-1-antitrypsin (Calbiochem, La Jolla, Calif.) in 200 μl phosphate buffered saline in place of angiostatin and stents were loaded as before.

plaque formation. Plaque morphometry was assessed as in Example 2, with results summarized as Table 5.

TABLE 5

Plaque formation after in vivo stent implantation and release of an elastase inhibitor.

| | Intima to media ratio |
|---|---|
| Control | 1.981 ± 0.080 |
| AAT | 1.322 ± 0.060 * |

Ratio of intimal area to medial area 28 days after stent implantation for control stents or stents releasing an elastase inhibitor (AAT), (mean ± SE), * denotes P = 0.0001 vs. controls.

Conclusions. Stent based local release of an inhibitor of extracellular matrix cleavage reduces plaque progression after stenting. This strategy works in any stent design for local release of the agent. Polymers, grooved stents, and anchoring are not necessary to achieve these effects, but are presented here for simplicity. The same effects is accomplished via any stent-based local release strategy and while this example presents use of MT as a specific agent, any factor to inhibit elastase or matrix metalloproteinases could be substituted with comparable result (i.e. the example demonstrates efficacy of the class of agents).

EXAMPLE 5

Stent-Based Release of Nicotine or Nicotinic Receptor Agonist Limits In-stent Plaque Progression microsphere/stent preparation. Microspheres were prepared as above (Example 2) except loaded with 30.0 mg Nicotine (Sigma Chemical, St Louis, Mo.) (to achieve a calculated daily load release of 0.1 mg/ml) in 200 μl phosphate buffered saline in place of angiostatin and stents were loaded as before.

plaque formation. Plaque morphometry was assessed as in Example 2, with results summarized as Table 6.

TABLE 6

Plaque formation after in vivo stent implantation and nicotine release.

| | Intima to media ratio |
|---|---|
| Control | 1.981 ± 0.080 |
| Nicotine | 1.377 ± 0.060 * |

Ratio of intimal area to medial area 28 days after stent implantation for control stents or stents releasing nicotine (mean ± SE), * denotes P = 0.0001 vs. controls.

Conclusions. Stent based local release of nicotine reduces plaque progression after stenting. This strategy works in any stent design for local release of the agent. Polymers, grooved stents, and anchoring are not necessary to achieve these effects, but are presented here for simplicity. The same effects is accomplished via any stent-based local release strategy.

EXAMPLE 6

Stent-Based Release of Transforming Growth Factor β Can Limit In-stent Plaque Progression microsphere/stent preparation. Microspheres were prepared as above, except loaded with 2.0 μg TGFβ1 (Oncogene Research, Boston, Mass.) in 200 μl pilphosphate buffered saline in place of angiostatin and stents were loaded as before.

plaque formation. Plaque morphometry was assessed as above, with results summarized as Table 7.

TABLE 7

Plaque formation after in vivo stent implantation and TGFβ1 release.

| | Intima to media ratio |
|---|---|
| Control | 1.981 ± 0.080 |
| TGFβ1 | 1.803 ± 0.053 * |

Ratio of intimal area to medial area 28 days after stent implantation for control stents or stents releasing transforming growth factor β1 (TGFβ1), (mean ± SE), * denotes P = 0.004 vs. controls.

Stent based local release of transforming growth factor β or other agonist of transforming growth factor β receptors or downstream signaling reduces plaque progression after stenting. This strategy will work in any stent design for local release of the agent. Polymers, grooved stents, and anchoring are not necessary to achieve these effects, but are presented here for simplicity. The same effects could be accomplished via any stent-based local release strategy.

EXAMPLE 7

Stent-Based Release of an Angiotensin Pathway Inhibitor

Release of an inhibitor of angiotensin converting enzyme, angiotensin, angiotensin II, or angiotensin II receptors can limit in-stent plaque progression.

microsphere/stent preparation. Microspheres were prepared as above except loaded with 1.2 mg of the angiotensin II receptor inhibitor perindoprilate in 200 µl phosphate buffered saline in place of angiostatin and stents were loaded as before.

plaque formation. Plaque morphometry was assessed as above, with results summarized as Table 8.

TABLE 8

Plaque formation after in vivo stent implantation and release of an angiotensin II receptor inhibitor.

|  | Intima to media ratio |
|---|---|
| Control | 1.981 ± 0.080 |
| ATIIr | 1.730 ± 0.090 * |

Ratio of intimal area to medial area 28 days after stent implantation for control stents or stents releasing of an angiotensin II receptor inhibitor, (ATIIr), (mean ± SE), * denotes P = 0.02 vs. controls.

Stent based local release of an inhibitor of angiotensin converting enzyme, angiotensin, angiotensin II, or angiotensin II receptors or downstream signaling reduces plaque progression after stenting. This strategy will work in any stent design for local release of the agent. Polymers, grooved stents, and anchoring are not necessary to achieve these effects, but are presented here for simplicity. The same effects could be accomplished via any stent-based local release strategy.

EXAMPLE 8

Stent-Based Release of a Pro-Apoptotic Factor microspherelstent preparation. Microspheres were prepared as above except loaded with 10 µg Fas ligand (Oncogene Research, Boston, Mass.) in 200 µl phosphate buffered saline in place of angiostatin and stents were loaded as before.

plaque formation. Plaque morphometry was assessed as above, with results summarized as Table 9.

TABLE 9

Plaque formation after in vivo stent implantation and release of Fas ligand.

|  | Intima to media ratio |
|---|---|
| Control | 1.981 ± 0.080 |
| Fas ligand | 1.356 ± 0.053 * |

Ratio of intimal area to medial area 28 days after stent implantation for control stents or stents releasing Fas Ligand, (mean ± SE), * denotes P < 0.05 vs. controls.

Stent based local release of a pro-apoptotic factor such as fas-ligand reduces plaque progression after stenting. This strategy will work in any stent design for local release of the agent. Polymers, grooved stents, and anchoring are not necessary to achieve these effects, but are presented here for simplicity. The same effects could be accomplished via any stent-based local release strategy, and while this example presents use of Fas ligand as a specific agent, any pro-apoptotic factor could be substituted with comparable result (i.e. the example demonstrates efficacy of the class of agents).

EXAMPLE 9

Stent-Based Release of Fibroblast Growth Factor microsphere/stent preparation. Microspheres were prepared as above except loaded with 200 ng acidic FGF (Calbiochem, La Jolla, Calif.) and 1280 units filtered endotoxin-free heparin (Sigma Chemical, St Louis, Mo.) as a stabilizer in 200 µl phosphate buffered saline in place of angiostatin and stents were loaded as before.

plaque formation. Plaque morphometry was assessed as above, with results summarized as Table 10.

TABLE 10

Plaque formation after in vivo stent implantation and release of acidic FGF.

|  | Intima to media ratio |
|---|---|
| Control | 1.981 ± 0.080 |
| FGF | 1.634 ± 0.051 * |

Ratio of intimal area to medial area 28 days after stent implantation for control stents or stents releasing of acidic FGF, (FGF), (mean ± SE), * denotes P = 0.004 vs. controls.

Stent based local release of fibroblast growth factor (acidic or basic, with or without heparin), any pro-endothelialization growth factor or related downstream signaling reduces plaque progression after stenting. This strategy will work in any stent design for local release of the agent. Polymers, grooved stents, and anchoring are not necessary to achieve these effects, but are presented here for simplicity. The same effects could be accomplished via any stent-based local release strategy.

EXAMPLE 11

Stent-Based Release of Thrombin Pathway Inhibitors microsphere/stent preparation. Microspheres are prepared as above except loaded with D-Phe-Pro-Arg chloromethyl ketone (PPACK, Calbiochem), which is the prototype of a class of synthetic tripeptides that form covalent complexes with thrombin, (Calbiochem, La Jolla, Calif.) in 200 µl phosphate buffered saline in place of angiostatin and stents were loaded as before. PPACK irreversibly inhibits thrombin by alkylating the active center histidine residue. Since thrombin and thrombin receptor-activating peptide (TRAP)-induced DNA synthesis are potently inhibited by PD98059 (Calbiochem, La Jolla, Calif.), an inhibitor of ERK phosphorylation, this inhibitor or others of its class can be used alone or in combination to inhibit thrombin-mediated plaque progression after stenting. PD98059 is examined in the range from 100 nmol/l to 500 µmol/L daily release (optimal typically in the range of 10 µmol/L). PPACK is evaluated in a range from 0.1 nmol/L to 10 µmol/L daily release (with typical use at 10 nmol/L in vitro).

plaque formation. Plaque morphometry is assessed as above.

EXAMPLE 12

Stent-Based Gene Transfer microsphere/stent preparation. Microspheres were prepared as above (example 2) except loaded with 200 µl of a 1.0 mg/ml solution of a plasmid encoding *E. coli* beta-galactosidase as a marker under the control of the cytomegalovirus promoter with a 2:1 charge ratio of Superfect (400 µl of stock 1.2 mg/ml, Qiagen) added as a transfection agent (10 µl undiluted) (Calbiochem, La Jolla, Calif.) in 200 µl phosphate buffered saline in place of angiostatin.

Gene expression. Gene expression was confirmed functionally on cross-sections obtained as for plaque morphometry 7 days after stent deployment. Beta galactosidase expression was visualized using X-gal staining (Sigma, St. Louis, Mo.). The results showed specific expression of the encoded enzyme.

Conclusions. Stent-based gene transfer of DNA, RNA, ribozyme, hybrids, or derivatives can be afforded at levels to achieve therapeutic benefit. This strategy will work in any stent design for local release of the agent. Polymers, grooved stents, and anchoring are not necessary to achieve these effects, but are presented here for simplicity. The same effects could be accomplished via any stent-based local release strategy, and while this example presents use of beta-galactosidase as a specific agent, any DNA, RNA, ribozyme, hybrid, or derivative could be substituted alone or in combination with comparable result (ie the example demonstrates efficacy of the class of agents).

EXAMPLE 13

Stent-Based Gene Transfer to Limit Plaque Progression microsphere/stent preparation. Microspheres are prepared as above except loaded with 20 µl of a 1.0 mg/ml solution of a plasmid encoding human thrombomodulin under the control of the cytomegalovirus promoter with a 4:1 charge ratio of Superfect added as a transfection agent (10 µl undiluted) (Calbiochem, La Jolla, Calif.) in 200 µl phosphate buffered saline in place of angiostatin.

plaque formation. Plaque morphometry is assessed as above, with gene expression also confirmed antigenically or functionally.

EXAMPLE 14

Stent-Based Delivery of Passively Entangled Noncovalently Bound Rapamycin to Limit Plaque Progression stent preparation. BX-velocity stents (Cordis, Miami, Fla.) are derivatized as above with a silane linker. The stent is placed within an outer tube which rests flush against the stent outer surface and is open at either end. A glycerol solution or other viscous solution is instilled to fill all spaces. The glycerol is allowed to drain by gravity and the stent is washed and immediately drained with sterile water, allowing some traces of glycerol to remain at the stent-tube interface. The outer surface of the stent and the adjacent sites are thus blocked from incubation, as a solution with a polymerization chain blocker or terminator is instilled and linked to the exposed surface of the stent. In the present case, such a terminator is polyethylene glycol (PEG) monoacrylate (MW200), which is anchored under exposure to UV-A source for 15 minutes. The stent is then removed from the cylinder and washed repeatedly to remove glycerol and unreacted chain blocker. The stent is then immersed in a sterile highly viscous solution containing PEG (MW 8000), PEG dimethacrylate (MW1200), and star-polymer PEG multi-methacrylates together with rapamycin at an effective dose for post-stenting restenosis. The stent is placed within an outer tube which allows a gap of 30 microns between the stent and the inner wall of the cylinder (although other thicknesses are valid as well). The gel is then polymerized under UV-A for 30 minutes to anchor rapamycin passively to the outer surface of the stent and the shoulders of the stent. Unreacted solution is removed by washing and the stent is lyophillized for use.

plaque formation. Plaque morphometry is assessed as above, with gene expression also confirmed antigenically or functionally.

EXAMPLE 15

Stent-Based Delivery of Chelated Noncovalently Bound Rapamycin to Limit Plaque Progression stent preparation. BX-velocity stents (Cordis, Miami, Fla.) are derivatized as above with a silane linker. The stent is placed within an outer tube which rests flush against the stent outer surface and is open at either end. A glycerol solution or other viscous solution is instilled to fill all spaces. The glycerol is allowed to drain by gravity and the stent is washed and immediately drained with sterile water, allowing some traces of glycerol to remain at the stent-tube interface. The outer surface of the stent and the adjacent sites are thus blocked from incubation, as a solution with a polymerization chain blocker or terminator is instilled and linked to the exposed surface of the stent. In the present case, such a terminator is polyethylene glycol (PEG) monoacrylate (MW200), which is anchored under exposure to UV-A source for 15 minutes. The stent is then removed from the cylinder and washed repeatedly to remove glycerol and unreacted chain blocker. The stent is then immersed in a highly viscous solution containing PEG (MW 8000), PEG dimethacrylate (MW1200), and a carrier which contains a methacrylate link and self assembles to chelate and carry rapamycin via some combination of ionic, hydrogen bonds, and van der waals forces together with rapamycin at an effective dose for post-stenting restenosis. The gel is then polymerized under UV-A for 30 minutes to anchor rapamycin passively to the outer surface of the stent and the shoulders of the stent. Unreacted solution is removed by washing and the stent is lyophillized for use.

plaque formation. Plaque morphometry is assessed as above, with gene expression also confirmed antigenically or functionally.

EXAMPLE 14

Stent-Based Delivery of Noncovalently Bound RheoPro to Limit Plaque Progression stent preparation. BX-velocity stents (Cordis, Miami, Fla.) are derivatized as above with a silane linker. The stent is placed within an outer tube which rests flush against the stent outer surface and is open at either end. A glycerol solution or other viscous solution is instilled to fill all spaces. The glycerol is allowed to drain by gravity and the stent is washed and immediately drained with sterile water, allowing some traces of glycerol to remain at the stent-tube interface.

The outer surface of the stent and the adjacent sites are thus blocked from incubation, as a solution with a polymerization chain blocker or terminator is instilled and linked to the exposed surface of the stent. In the present case, such a terminator is polyethylene glycol (PEG) monoacrylate (MW200), which is anchored under exposure to UV-A source for 15 minutes. The stent is then removed from the cylinder and washed repeatedly to remove glycerol and unreacted chain blocker. The stent is then immersed in a sterile highly viscous solution containing PEG (MW 8000), PEG dimethacrylate (MW1200), and star-polymer PEG multi-methacrylates together with RheoPro at an effective dose for post-stenting restenosis. The stent is placed within an outer tube which allows a gap of 30 microns between the stent and the inner wall of the cylinder (although other thicknesses are valid as well). The gel is then polymerized under UV-A for 30 minutes to anchor RheoPro passively to the outer surface of the stent and the shoulders of the stent. Unreacted solution is removed by washing and the stent is lyophillized for use.

plaque formation. Plaque morphometry is assessed as above, with gene expression also confirmed antigenically or functionally.

What is claimed is:

1. A method for inhibiting restenosis, the method comprising:
   implanting in the lumen of a vessel a stent comprising rapamycin as an anti-restenotic agent, wherein said stent comprises channels on one or both of the adluminal and abluminal surfaces, wherein contained within said channels is a matrix of microspheres in which said anti-restenotic agent is entrapped; said stent being ensheathed in a gel covalently bound to the stent surface, which gel fills unoccupied spaces within the channels and between said microspheres, wherein said anti-restenotic agent is released at the site of implantation, thereby inhibiting restenosis.

2. The method according to claim 1, wherein said restenosis is inhibited by at least about 10% over a period of about 4 weeks.

3. The method according to claim 1, wherein said restenosis is inhibited by at least about 25% over a period of about 4 weeks.

4. The method according to claim 1, wherein said stent is formed of a biologically compatible metal or a shape memory plastic.

5. The method according to claim 1, wherein said stent is a polymeric biodegradable or erodible stent.

6. The method according to claim 1, wherein said channels are from 10 to 200 μm in depth.

7. The method according to claim 1, wherein said channels extend end to end, or the entire circumference of the stent.

8. The method according to claim 1, wherein said channels are adluminal.

9. The method according to claim 1, wherein said channels are abluminal.

10. The method according to claim 1, wherein said channels are at least about 10 μm in width and not more than about 75% of the total width of the stent element.

11. The method according to claim 1, wherein said stent surface is modified with an adhesion agent covalent binding.

12. The method according to claim 11, wherein said stent is comprised of a biologically compatible metal, and said adhesion agent is a silane coupling reagent.

13. The method according to claim 1, wherein said microspheres are of about 5 to about 100 μm in diameter.

14. The method according to claim 1, wherein said microspheres are of about 50 to 100 μm in diameter.

15. The method according to claim 1, wherein said matrix is comprised of a biodegradable polymer.

16. The method according to claim 20, wherein said biodegradable polymer comprises one or more of D-lactic acid, L-lactic acid, racemic lactic acid, glycolic acid and polycaprolactone.

17. The method according to claim 1, wherein said matrix is comprised of a biocompatible, non-biodegradable polymer.

18. The method according to claim 1, wherein said gel comprises methacrylate.

19. The method according to claim 1, wherein said anti-restenotic agent inhibits in-stent restenosis.

20. A drug delivery stent for inhibiting restenosis, comprising:
   a stent capable of delivering an anti-restenotic agent at the site of implantation; and an anti-restenotic agent, wherein said stent comprises channels on one or both of the adluminal and abluminal surfaces, wherein contained within said channels is a matrix of microspheres in which said anti-restenotic agent is entrapped, said stent being ensheathed in a gel covalently bound to the stent surface, which gel fills unoccuppied spaces within the channels and between said microspheres; and wherein said anti-restenetic agent is released at the site of implantation, thereby inhibiting restenosis.

21. The drug delivery stent according to claim 20, wherein said channels are from 10 to 200 μm in depth.

22. The drug delivery stent according to claim 20, wherein said channels extend end to end, or the entire circumference of the stent.

23. The drug delivery stent according to claim 20, wherein said channels are adluminal.

24. The drug delivery stent according to claim 20, wherein said channels are abluminal.

25. The drug delivery stent according to claim 20, wherein said channels are at least about 10 μm in width and not more than about 75% of the total width of the stent element.

26. The drug delivery stent according to claim 20, wherein said stent surface is modified with an adhesion agent covalently bound.

27. The drug delivery stent according to claim 26, wherein said stent is comprised of a biologically compatible metal, and said adhesion agent is a silane coupling reagent.

28. The drug delivery stent according to claim 20, wherein said microspheres are of about 5 to about 100 μm in diameter.

29. The drug delivery stent according to claim 20, wherein said microspheres are of about 50 to 100 μm in diameter.

30. The drug delivery stent according to claim 20, wherein said gel comprises methacrylate.

* * * * *